United States Patent [19]
Clement et al.

[11] Patent Number: 5,681,336
[45] Date of Patent: Oct. 28, 1997

[54] THERAPEUTIC DEVICE FOR TREATING VIEN GRAFT LESIONS

[75] Inventors: Thomas J. Clement, Redmond; David C. Auth, Kirkland, both of Wash.; Maurice Buchbinder, San Diego, Calif.

[73] Assignee: Boston Scientific Corporation, Redmond, Wash.

[21] Appl. No.: 524,591

[22] Filed: Sep. 7, 1995

[51] Int. Cl.⁶ .......................... A61B 17/22; A61B 17/14; A61M 29/00
[52] U.S. Cl. .................. 606/159; 606/180; 604/96
[58] Field of Search ................. 606/1, 127, 167, 606/159, 180; 604/96–104; 128/657, 772

[56] References Cited

U.S. PATENT DOCUMENTS

| | | |
|---|---|---|
| 4,445,509 | 5/1984 | Auth . |
| 4,679,557 | 7/1987 | Opie et al. . |
| 4,790,813 | 12/1988 | Kensey ................................. 606/159 |
| 4,846,174 | 7/1989 | Willard et al. . |
| 4,926,858 | 5/1990 | Gifford, III et al. . |
| 4,950,238 | 8/1990 | Sullivan . |
| 4,990,134 | 2/1991 | Auth . |
| 5,102,390 | 4/1992 | Crittenden et al. . |
| 5,135,482 | 8/1992 | Nerasher ............................... 606/159 |
| 5,318,576 | 6/1994 | Plassche et al. ....................... 606/159 |

FOREIGN PATENT DOCUMENTS

| | | | |
|---|---|---|---|
| 0229620 | 7/1987 | European Pat. Off. ............... | 606/159 |
| 416734 B1 | 6/1995 | European Pat. Off. . | |

*Primary Examiner*—Glenn Dawson
*Attorney, Agent, or Firm*—Cowan, Liebowitz & Latman P.C.

[57] ABSTRACT

A rotational ablation device for use in medical applications which are designed to reduce lesions, particularly vein-graft lesions, within blood vessels, the device includes a distal balloon located at the end of a guide wire, a proximal balloon having a cuff surrounding a guide catheter, an inflation lumen for use in inflating a distal balloon on the guide catheter, one or more rotating burrs used in conjunction with a helical drive system surrounding the guidewire; a suction system to remove ablated lesion material; and a control console to provide for the necessary control of the various systems of the device.

18 Claims, 4 Drawing Sheets

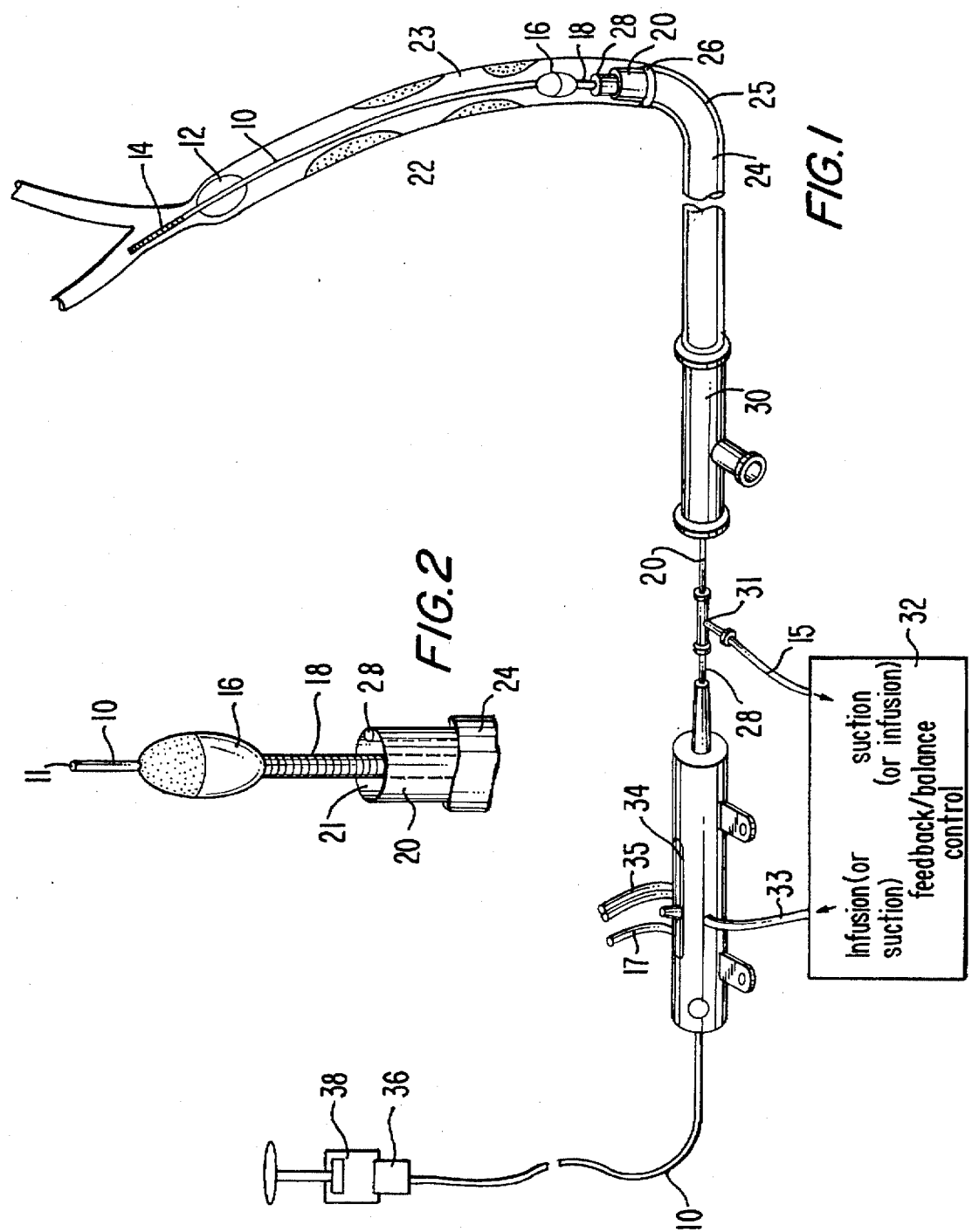

THERAPEUTIC DEVICE FOR TREATING VIEN GRAFT LESIONS

FIELD OF THE INVENTION

This invention relates to the field of mechanical devices which are useful in medical applications and which are capable of differentially cutting abnormal deposits from within a patient's vessels. More particularly, the present invention relates to a rotational ablation device for use in connection with the reduction of vein-graft lesions.

BACKGROUND OF THE INVENTION

Various prior art devices are known which allow a user to insert a catheter/guide wire means into a body cavity or blood vessel to allow the user to deliver an inflatable balloon, cutting device or other therapeutic means to the area of need. In carrying out such procedures, which may be generally described as either angioplasty or atherectomy, the object is generally to effect the opening of a stenotic segment of a blood vessel.

Angioplasty uses an inflatable device positioned in the artery to dilate the lumen at the stenosis. A typical angioplasty device is disclosed in Bhate et al., U.S. Pat. No. 4,896,669. The angioplasty device of Bhate et al. includes an inflatable balloon which is attached to the distal end of a hollow catheter. The proximal end of the catheter is attached to a fluid source, providing fluid communication between the balloon and the fluid source.

To treat an arterial stenosis, the Bhate et al balloon is introduced into the artery in a deflated state and guided through the artery over a guidewire to a position adjacent to the stenosis. Fluid from the fluid source is then infused into the balloon via the catheter to inflate the balloon. As the balloon expands, it dilates the lumen of the artery. The balloon is then deflated and removed from the artery.

While effective for dilating the lumen at the stenosis, angioplasty devices such as the Bhate et al. device do not remove plaque from the artery. Consequently, the residual plaque either remains in place at the point of the stenosis or breaks off and migrates to other locations in the blood stream. In either case, the plaque remains a continuing threat to create blockages in the circulatory system. To address the shortcomings of angioplasty, a procedure termed atherectomy has been developed, in which plaque is cut and removed from the blood vessel.

An atherectomy procedure typically includes inserting a guidewire into the affected artery and advancing a hollow cutting device over the guidewire until the cutting device is positioned adjacent to the stenosis. The cutting device is then advanced into the stenosis to cut a channel through the plaque, thereby increasing blood flow through the artery. The resulting plaque fragments are either removed from the blood stream by drawing them into the hollow cutting device or allowed to flow through the patient's blood system to be removed by the patient's circulatory system.

A number of atherectomy devices are known in the art. For example, Auth, U.S. Pat. No. 4,990,134 describes a rotating mechanical system which is itself an improvement upon the device described in Auth, U.S. Pat. No. 4,445,509. The Auth '134 patent teaches the use of an ellipsoidal cutting head, or burr, which cutting head is coated with tiny diamond chips (shovels). The cutting head rotates and causes differential cutting, whereby the cutting head differentiates between inelastic plaque, which is removed, and elastic arterial tissue, which remains undamaged. More specifically, it is taught that a tip (burr) of the type described, operating at a tip velocity of at least about 40 ft./sec., is able to cut inelastic material at a high removal rate, while generating microscopic particles (on the order of 5 microns or less) and leaving behind a tissue base having a smooth appearance on the surface of the wall of the vessel from which an abnormal deposit has been removed.

Known atherectomy devices are primarily directed to removing plaque from arterial surfaces. However, there are instances where plaque occurs on a venous surface, such as in the case where venous grafts used in a bypass have stenosed. Several attributes of vein-graft lesions distinguish such lesions from native coronary artery lesions. First, the nature of the lesion can be a softer, less organized material and is typically covered by a fibrous cap. Second, the diameter of the lumen is typically larger than that encountered in native coronary arteries.

Due to the inherent differences between the nature of native coronary arterial lesions and vein-graft lesions, prior art devices have been found to be less than satisfactory in the treatment of such vein-graft lesions. The device of the present invention incorporates a number of new concepts to expand the benefits of rotational ablation into the area of vein-graft lesions.

OBJECTS OF THE INVENTION

It is an object of the present invention to provide for a rotational ablation device for use in medical applications which address the inherent differences between native coronary arterial lesions and vein-graft lesions.

It is also an object of the present invention to provide for rotational ablation devices for use in medical applications which are specifically designed to remove or reduce vein-graft lesions.

It is a further object of the present invention to provide for improved rotational ablation devices for use in medical applications which are particularly designed to reduce vein-graft lesions in such a manner that the resultant ablated lesion material is effectively removed from the body.

These and other objects of the invention will become apparent from the following discussion of the invention.

SUMMARY OF THE INVENTION

The present invention provides for a rotational ablation device for use in medical applications designed to reduce lesions, particularly vein-graft lesions, within blood vessels. The rotational ablation device is provided with a guidewire which comprises a hypo-tube having an inflation lumen to inflate a distal balloon located at the end of the guide wire, suction means to remove the ablated lesion material from the body, one or more rotating burrs which operate in conjunction with the aforesaid guidewire and which employ the aforesaid guidewire as a rail, and a proximal balloon which comprises a cuff surrounding a guide catheter. A feedback balance control system operating in conjunction with a pressure transducer means monitors the vessel pressure and provides sufficient infusion, and an accompanying control console provides the necessary control means for the balloon pressures and other operating functions of the ablation, infusion and suction means.

BRIEF DESCRIPTION OF THE DRAWINGS

FIG. 1 is a schematic representation of a typical configuration of a rotational ablation device of the present invention illustrating the various elements and depicting a multi-lumen channel surrounding a rotating helical drive;

FIG. 2 is a schematic representation of a portion of the rotational ablation device of FIG. 1 showing the relative configuration of the rotating helical drive, the burr, the suction lumen and the infusion lumen;

DETAILED DESCRIPTION OF THE INVENTION

Figure 3:
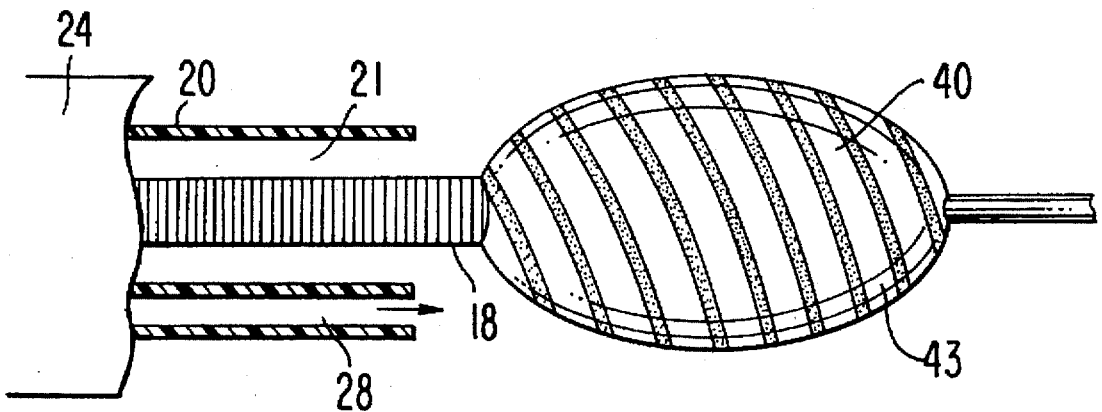
FIG. 3 is a schematic representation of one embodiment of a preferred configuration of a portion of the rotational ablation device of FIG. 1 depicting a fluted symmetrical burr.

The device of the present invention has features which address the differences found between vein-graft lesions and native coronary arterial lesions. Due to the nature of vein-graft lesions, a predictable release of fine particulate cannot be assumed, as it can be in the treatment of "organized" native artery lesions by rotational ablation. Therefore, the device of the present invention incorporates the use of distal and proximal balloons to isolate the region of treatment from the rest of the coronary arterial system. The proposed device also incorporates suction means to remove the ablated lesion material from the body. To prevent collapse of the graft, a feedback/balance control system is also incorporated, to provide sufficient infusion. A pressure transducer is also employed to monitor actual vessel pressure. A distal balloon is located on a guidewire, which guidewire is constructed of a hypo-tube with an inflation lumen to inflate the balloon. The guidewire also constitutes a "rail" to guide the rotating burr through the lesion. Optionally, additional infusion of the distal vessel bed may be accomplished through a lumen of the guidewire. The proximal balloon comprises a cuff of the guide catheter. Control of the balloon pressures is carried out by means of an accompanying control console.

The larger lumen encountered in vein-graft lesions is addressed by using an expandable burr, eccentric burr, or existing diamond coated burr technology, such as described in U.S. Pat. No. 4,990,134, incorporated herein by reference. In the device of the present invention the burrs may be rotated at lower speeds than are used with high speed ablation devices, to compensate for heat or imbalance. High rotational speed to minimize particle size is not as critical for the effective operation of the device of the present invention as it is in native artery rotational ablation, since particulate matter is recovered.

A preferred embodiment of the present invention is shown in FIGS. 1 and 2. The system comprises a guidewire 10 which preferably consists of a hypo-tube having a sufficient lumen 11 to inflate a distal balloon 12 located at the distal end of the guidewire proximal to a spring wire tip 14. Tracking over guidewire 10 and operating in conjunction therewith is a rotating burr 16 attached to a helical drive shaft 18. A dual lumen sheath or catheter 20, which has a first lumen 21 through which helical drive shaft 18 extends, enters vessel 22 through a guide catheter 24. Guide catheter 24 is provided with a balloon cuff 26 at the distal end of guide catheter 24, which balloon cuff 26 provides the means necessary to seal the proximal inner surface 23 of vessel 22 against the outer surface of guide catheter 24 and, therefore, to isolate the segment of the vessel 22 to be ablated.

Catheter 20 can be provided with a second, interior infusion lumen 28 through which the interior pressure of the vessel 22 can be maintained using saline or other infusate. The proximal ends of the catheter 20 and guide catheter 24 are provided with one or more "Y" connectors 30 and 31 to provide the means necessary for the inflation of the guide catheter balloon cuff 26 and for infusion and suction through catheter lumens 28 and 21. A lumen 25 in guide catheter 24 provides fluid communication between balloon cuff 26 and Y connector 30.

Infusion lumen 28 and first catheter lumen 21 are each operatively connected to and through a feedback control means 32. Y connector 31 is connected to feedback control means 32 through suction/infusion connector 15, and prime mover 34 is connected to feedback control means 32 through infusion/suction connector 33. The prime mover 34 is connected to an air supply through air supply/drive connector 17 and to a fiber optic/tachometer means through connector 35. The proximal end of the guidewire is connected to a coupler 36 which is attached to an inflation means 38 for use in inflating the distal balloon 12.

With reference to FIG. 2, the distal portion of the ablation means of the system is shown in more detail.

Figure 4:
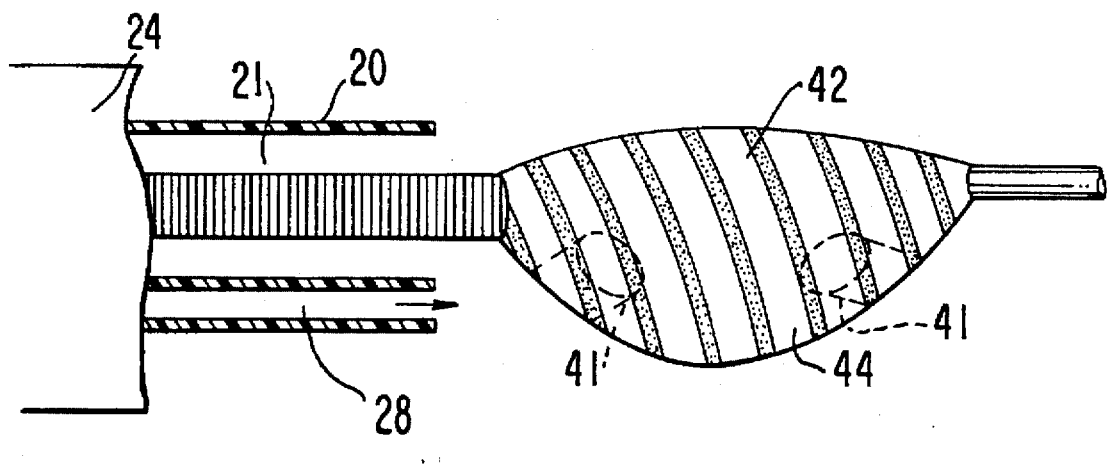
FIG. 4 is a schematic representation of another embodiment of a preferred configuration of a portion of the rotational ablation device of FIG. 1 depicting a fluted eccentric burr.

FIGS. 3 and 4 depict alternate embodiments of an ablation burr useful according to the invention. In FIG. 3 a fluted symmetrical burr 40 is attached to the distal end of helical drive shaft 18. Helical drive shaft 18 is encompassed by a multiple lumen sheath 20, which includes first lumen 21 and infusion lumen 28, all shown at the distal point of exit from guide catheter 24. The burr 42 shown in FIG. 4 is similar to burr 40 but is asymmetrical. When burr 42 rotates, it creates a passageway having a diameter greater than the burr maximum diameter. Burrs 40 and 42 have external cutting edges or surfaces 43 and 44, respectively, which can comprise flutes or abrasive material. Also, optionally each of burrs 40 and 42 could have infusion openings 41, which would be in fluid communication with a lumen in helical drive 18.

Figure 5:
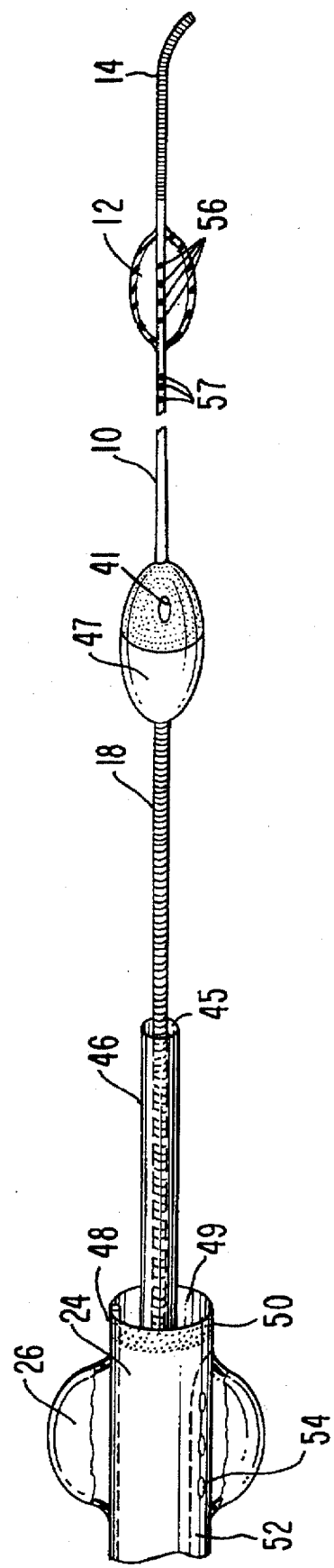
FIG. 5 is a schematic representation of a portion of another preferred configuration of the rotational ablation device of FIG. 1 depicting the relative configuration of the suction lumen, rotating helical drive, burr, guidewire and balloon, wherein the guidewire catheter and catheter lumen are used for infusion.

A slight variation of the above-described embodiment of the invention is represented by the schematic representation in FIG. 5. A diamond chip-plated burr 47 is attached to the distal end of a helical drive shaft 18. Drive shaft 18 is encompassed by a sheath 46 having a single lumen 45 for infusion. The annular space 49 between sheath 46 and guide catheter 24 forms a channel for suction removal of debris. Guide catheter 24 may optionally have a pressure transducer lumen 48, which provides for fiber optic or other sensing means to monitor the pressure within the vessel. The distal end of the guide catheter can optionally be provided with a radiopaque marker 50. Surrounding the distal end of the guide catheter is balloon cuff 26 which is inflated by means of a balloon inflation channel 52 which allows for inflation of the cuff through ports 54. Alternatively, balloon cuff 26 could be inflated with an inflation medium containing contrast, whereby balloon cuff 26 would also function as a radiopaque marker.

The rotating burr 47 and helical drive shaft 18 track over guidewire 10 which comprises a lumen 11 whose primary purpose is to provide an inflation means to the distal balloon 12 through ports 56. Balloon 12 can be inflated with conventional medium such as, for example, saline solution, contrast, or carbon dioxide. The guidewire lumen 11 is also provided with ports 57 to allow an alternative manner for infusion of the distal segment of the vessel to be ablated.

Figure 6:
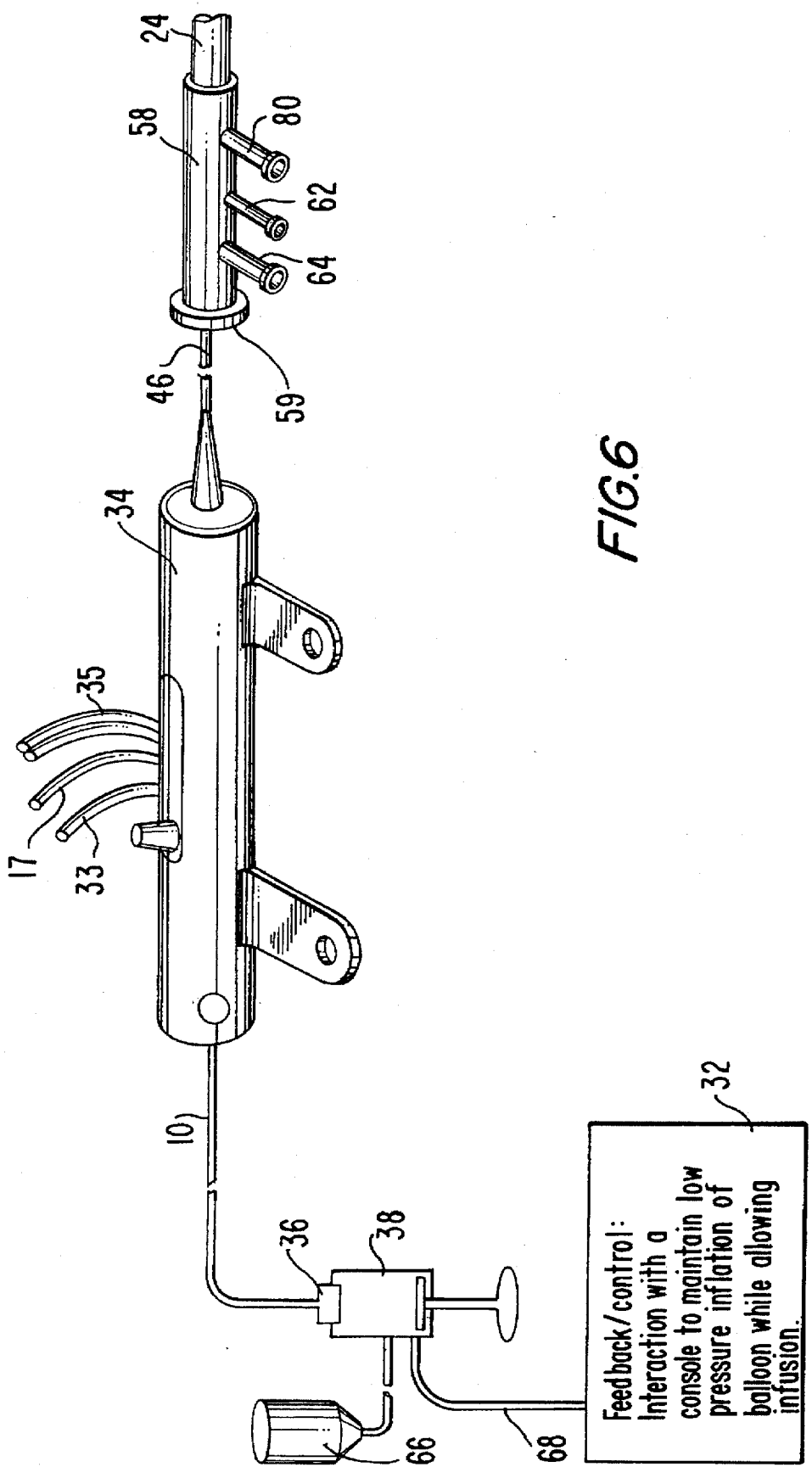
FIG. 6 is a schematic representation of a preferred embodiment of the proximal portion of the rotational ablation device of FIG. 1 depicting the configuration of the various infusion, suction and control ports.

FIG. 6 is a schematic representation of a preferred embodiment of the proximal portion of the rotational ablation system of the invention, showing the configuration of the various infusion, suction and control ports. The proximal end of the guide catheter 24 is shown attached to a manifold 58, which is provided with an entry port 60 to provide inflation of the guide catheter balloon cuff 26, a port 62 to provide access to the pressure transducer channel 48, and a port 64 to provide suction through the guide catheter 24. The manifold 58 is sealingly connected through a Tuohy-Borst gland 59 to the sheath 46, which is in turn connected to infusion connector 33, air supply/drive control connector 17, and fiberoptic/tachometer means connector 35, for the rotation of the helical drive 18 and burr 47, through which passes the guidewire 10, which is connected to the inflator 38 by means of a coupler 36. The inflator 38 is provided with a source of media 66 for inflation of the distal balloon and is interconnected via a feedback control means 68 to a control console 70 to maintain low pressure inflation of the balloon while allowing infusion into the vessel.

The rotational burr or cutting head provided for in the ablation device of the present invention may be one of any possible number of conventionally available configurations, including standard diamond plated burrs, expandable burrs, fluted burrs, eccentric burrs, burrs with side holes for flushing or infusion, and metal or nylon wire brush burrs. See, for example, U.S. Pat. Nos. 4,445,509 and 4,990,134, both of which are incorporated herein by reference.

It will be understood by one skilled in this art that the device of the present invention may also effectively employ a multitude of burrs rather than just one burr.

The hypo-tube which comprises the guidewire in the rotational ablation device of the present invention will generally have an OD of from about 0.009 to 0.020 inches.

It will be further apparent to one skilled in this art that the improvements provided for in the present invention, while described with relation to certain specific physical embodiments also lend themselves to being applied in other physical arrangements not specifically provided for herein, which are nonetheless within the spirit and scope of the invention taught here. The technology disclosed herein can be used in connection with blockages in other human body vessels or passageways.

LIST OF ELEMENTS

| No. | Element |
|---|---|
| 10 | guidewire |
| 11 | guidewire lumen |
| 12 | distal balloon |
| 14 | spring wire tip |
| 15 | suction/infusion connector |
| 16 | rotating burr |
| 17 | air supply |
| 18 | helical drive shaft |
| 20 | dual lumen catheters |
| 21 | first lumen |
| 22 | vessel |
| 23 | vessel inner surface |
| 24 | guide catheter |

-continued

LIST OF ELEMENTS

| No. | Element |
|---|---|
| 25 | guide catheter inflation lumen |
| 26 | balloon cuff |
| 28 | interior infusion lumen |
| 30 | "Y" connector |
| 31 | "Y" connector |
| 32 | feedback control means |
| 33 | infusion/suction connector |
| 34 | prime mover |
| 35 | fiberoptic/tachometer means connector |
| 36 | coupler |
| 38 | inflation means |
| 40 | symmetrical burr |
| 41 | infusion openings |
| 42 | asymmetrical burr |
| 43,44 | cutting surface |
| 45 | infusion lumen |
| 46 | sheath |
| 47 | burr |
| 48 | pressure transducer lumen |
| 49 | annular space |
| 50 | radiopaque marker |
| 52 | balloon inflation channel |
| 54,56 | inflation port |
| 57 | infusion holes |
| 58 | manifold |
| 59 | Tuohy-Borst gland |
| 60 | inflation port |
| 62 | pressure transducer port |
| 64 | suction port |
| 66 | media |

We claim:

1. A rotational ablation system to remove a stenosis within a blood vessel in a patient's body, which comprises
    a guidewire having proximal and distal ends, the distal end of the guidewire comprising a dilatation balloon and the guidewire having a hollow lumen for inflation of said dilatation balloon,
    rotational ablation means having a hollow flexible drive shaft and abrasive burr connected thereto, said drive shaft and abrasive burr fitting slidingly over said guidewire,
    a flexible sheath having a longitudinally extending lumen surrounding said flexible drive shaft, and
    a guide catheter through which the guidewire is inserted having proximal and distal ends, wherein an inflatable annular balloon is arranged on the outer surface of the distal end of the guide catheter.

2. The system of claim 1, wherein there is an annular space between the flexible sheath and the drive shaft and particulate matter is removed proximally through said annular space.

3. The system of claim 1, wherein the flexible sheath has a separate infusion lumen.

4. The system of claim 1, wherein the guide catheter has a separate lumen for inflation of the annular balloon.

5. The system of claim 1, wherein the rotational ablation means has one or more openings in fluid communication with the drive shaft and particulate matter is removed proximally through said opening or openings and said drive shaft.

6. The system of claim 1, wherein there is an annular space between the guide catheter and the flexible sheath and particulate matter is removed through said annular space.

7. The system of claim 1, which also comprises a feedback balance control system in operative connection with a pressure transducer means for monitoring vessel pressure and for providing sufficient infusion to the vessel through the guide catheter.

8. The system of claim 1, which also comprises an accompanying control console comprising control means for controlling balloon pressures.

9. The system of claim 1, wherein the distal end of the dilation guidewire also comprises infusion ports proximal to the balloon.

10. The system of claim 1, wherein the guidewire comprises a hypo-tube.

11. The system of claim 1, wherein the distal end of the guidewire is provided with spring tip means.

12. The system of claim 1, wherein the distal end of the guidewire is provided with a radiopaque marker.

13. The system of claim 1, wherein the rotational ablation means is symmetrical.

14. The system of claim 1, wherein the rotational ablation means is asymmetrical.

15. A method for removing a stenosis from a patient's blood vessel, which comprises the steps of:

(a) advancing a guide catheter having proximal and distal ends into patient's blood vessel until said distal end is positioned proximal to a stenosis, the guide catheter having an inflatable annular balloon arranged thereon in a deflated state;

(b) advancing through the guide catheter a guidewire having proximal and distal ends and an inflatable balloon at said distal end, the distal end of said guidewire being advanced until it is distal to the stenosis;

(c) advancing a rotational ablation means with a hollow flexible drive shaft and abrasive burr over the guidewire until the rotational ablation means is proximal to the stenosis;

(d) inflating the inflatable balloon on the guidewire;

(e) inflating the annular balloon on the guide catheter;

(f) advancing the rotational ablation means along the guidewire to generate particulate matter from the stenosis;

(g) removing said particulate matter; and (h) deflating both balloons.

16. The method of claim 15, wherein the blood vessel is a vein graft.

17. The method of claim 15, wherein step (e) is performed before step (d).

18. The method of claim 15, wherein steps (d) and (e) are performed substantially simultaneously.

* * * * *